(12) United States Patent  
Eaton et al.

(10) Patent No.: US 8,996,767 B2
(45) Date of Patent: Mar. 31, 2015

(54) MOBILE DEVICE CONTROL BASED ON SURFACE MATERIAL DETECTION

(75) Inventors: John D. Eaton, San Diego, CA (US); Hung-Hsin Wu, San Diego, CA (US); Jose R. Menendez, San Diego, CA (US); William T. Frantz, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 248 days.

(21) Appl. No.: 13/462,445

(22) Filed: May 2, 2012

(65) Prior Publication Data

US 2013/0297926 A1  Nov. 7, 2013

(51) Int. Cl.
*G06F 13/12* (2006.01)
*G06F 1/24* (2006.01)
*H04M 1/725* (2006.01)
*G01N 21/17* (2006.01)

(52) U.S. Cl.
CPC ...... *H04M 1/72569* (2013.01); *H04M 1/72572* (2013.01); *H04M 2250/12* (2013.01); *G01N 21/17* (2013.01)
USPC ............................................. 710/72; 713/100

(58) Field of Classification Search
CPC ................ H04M 1/72569; H04M 1/72572; H04M 2250/12; G01N 21/17
See application file for complete search history.

(56) References Cited

U.S. PATENT DOCUMENTS 6,225,901 B1 * 5/2001 Kail, IV ................... 340/539.11
7,325,445 B1   2/2008 Bowman
7,580,725 B2   8/2009 Delker et al.
7,675,414 B2 * 3/2010 Ray ......................... 340/539.26
7,738,921 B2 * 6/2010 Silverbrook et al. ......... 455/557
8,065,508 B2 * 11/2011 Rubin et al. ....................... 713/1
8,130,193 B2 * 3/2012 Flynt et al. ..................... 345/156
8,319,746 B1 * 11/2012 Ho et al. ......................... 345/173
8,392,007 B1 * 3/2013 Izo et al. ........................ 700/94
8,464,036 B2 * 6/2013 Rubin et al. ..................... 713/1
8,483,725 B2 * 7/2013 Kim et al. .................. 455/456.6

(Continued)

FOREIGN PATENT DOCUMENTS

EP   2275907 A2   1/2011
WO   2012099941   7/2012

OTHER PUBLICATIONS

International Search Report and Written Opinion—PCT/US2013/033596—ISA/EPO—Jun. 21, 2013.

*Primary Examiner* — Henry Tsai
*Assistant Examiner* — Jing-Yih Shyu
(74) *Attorney, Agent, or Firm* — Silicon Valley Patent Group LLP

(57) ABSTRACT

A mobile device uses sensor data related to the type of surface in contact with the mobile device to determine an action to perform. The sensors, by way of example, may be one or more of a microphone and noise generator, a light based proximity sensor, and pressure sensors, such as dielectric elastomers, configured to detect a texture of the surface, and/or pressure waves produced by setting the mobile device down or by a noise generator and reflected by the surface. The mobile device may identify the type of surface and perform the action based on the type of surface. The mobile device may further determine its location based on the sensor data and use that location to identify the action to be performed. The location may be determined using additional data, e.g., data not related to determining the type of surface with which the mobile device is in contact.

30 Claims, 4 Drawing Sheets

(56) References Cited

U.S. PATENT DOCUMENTS

| | | | |
|---|---|---|---|
| 8,483,772 B2 * | 7/2013 | Naftolin | 455/566 |
| 8,547,360 B2 * | 10/2013 | Posamentier | 345/174 |
| 8,558,809 B2 * | 10/2013 | Lee et al. | 345/173 |
| 2003/0093600 A1 * | 5/2003 | Perala et al. | 710/72 |
| 2004/0259536 A1 * | 12/2004 | Keskar et al. | 455/418 |
| 2006/0242434 A1 * | 10/2006 | Lee | 713/300 |
| 2008/0168267 A1 * | 7/2008 | Bolen et al. | 713/100 |
| 2009/0164772 A1 * | 6/2009 | Karkaria et al. | 713/100 |
| 2009/0247144 A1 * | 10/2009 | Jin et al. | 455/418 |
| 2010/0066546 A1 * | 3/2010 | Aaron | 340/601 |
| 2010/0090712 A1 * | 4/2010 | Vandermeijden | 324/658 |
| 2010/0131749 A1 * | 5/2010 | Kim et al. | 713/100 |
| 2010/0294938 A1 * | 11/2010 | Alameh et al. | 250/342 |
| 2011/0012840 A1 * | 1/2011 | Hotelling et al. | 345/173 |
| 2011/0086626 A1 * | 4/2011 | Kerr | 455/418 |
| 2011/0117903 A1 | 5/2011 | Bradley | |
| 2011/0141006 A1 * | 6/2011 | Rabu | 345/156 |
| 2012/0078999 A1 * | 3/2012 | Andrew et al. | 709/203 |
| 2012/0139393 A1 * | 6/2012 | Choi et al. | 310/366 |
| 2012/0173897 A1 * | 7/2012 | Karkaria et al. | 713/300 |
| 2012/0182539 A1 * | 7/2012 | Grokop et al. | 356/4.01 |
| 2012/0280917 A1 * | 11/2012 | Toksvig et al. | 345/173 |
| 2013/0145457 A1 * | 6/2013 | Papakipos et al. | 726/19 |
| 2013/0205131 A1 * | 8/2013 | Lee et al. | 713/100 |
| 2013/0232332 A1 * | 9/2013 | Naftolin | 713/100 |
| 2013/0244575 A1 * | 9/2013 | Forutanpour et al. | 455/41.1 |

* cited by examiner

MOBILE DEVICE CONTROL BASED ON SURFACE MATERIAL DETECTION

BACKGROUND

1. Background Field

Embodiments of the subject matter described herein are related generally to detecting a type of surface in contact with a mobile device, and more particularly, to performing an action based on the type of surface that is in contact with the mobile device.

2. Relevant Background

Many mobile devices, such as cellular or smart phones, tablet computers, etc. are capable of determining their general location using satellite positioning systems, such as the Global Positioning System (GPS), or using wireless signals for cellular towers or WiFi®. While such mobile devices can determine a general location, they cannot determine a precise location, e.g., whether the mobile device is at the user's work, car, home, movie theater, place of worship, etc., or whether the mobile device is on a table, a couch, on a carpeted floor, in a car, etc. The user of a mobile device often desires different device settings or actions to be performed based on specific locations, e.g., adjusting ringer volume depending on whether the mobile device is in a pocket, car, on a desk, or whether the mobile device is at the user's home, work, etc. Entering the desired device settings, however, is currently a manual process as the mobile device cannot determine its precise location.

SUMMARY

A mobile device uses sensor data related to the type of surface in contact with the mobile device to determine an action to perform. The sensors, by way of example, may be one or more of a microphone and noise generator, a light based proximity sensor, and pressure sensors, such as dielectric elastomers, configured to detect a texture of the surface, and/or pressure waves produced by setting the mobile device down or by a noise generator and reflected by the surface. The mobile device may identify the type of surface and perform the action based on the type of surface. The mobile device may further determine its location based on the sensor data and use that location to identify the action to be performed. The location may be determined using additional data, e.g., data not related to determining the type of surface with which the mobile device is in contact.

In one embodiment, a method includes receiving data from one or more sensors in a mobile device, wherein the data is related to a type of surface in contact with the mobile device; and performing an action based on the data related to the type of surface in contact with the mobile device.

In one embodiment, a mobile device includes one or more sensors; and a processor coupled to receive data from the one or more sensors, wherein the data is related to a type of surface in contact with the mobile device, the processor being configured to perform an action based on the data related to the type of surface in contact with the mobile device.

In one embodiment, a mobile device includes means for receiving data from one or more sensors in a mobile device, wherein the data is related to a type of surface in contact with the mobile device; and means for performing an action based on the data related to the type of surface in contact with the mobile device.

In one embodiment, a non-transitory computer-readable medium including program code to receive data from one or more sensors in a mobile device, wherein the data is related to a type of surface in contact with the mobile device; and program code to perform an action based on the data related to the type of surface in contact with the mobile device.

DETAILED DESCRIPTION

Figures 1A, 1B:
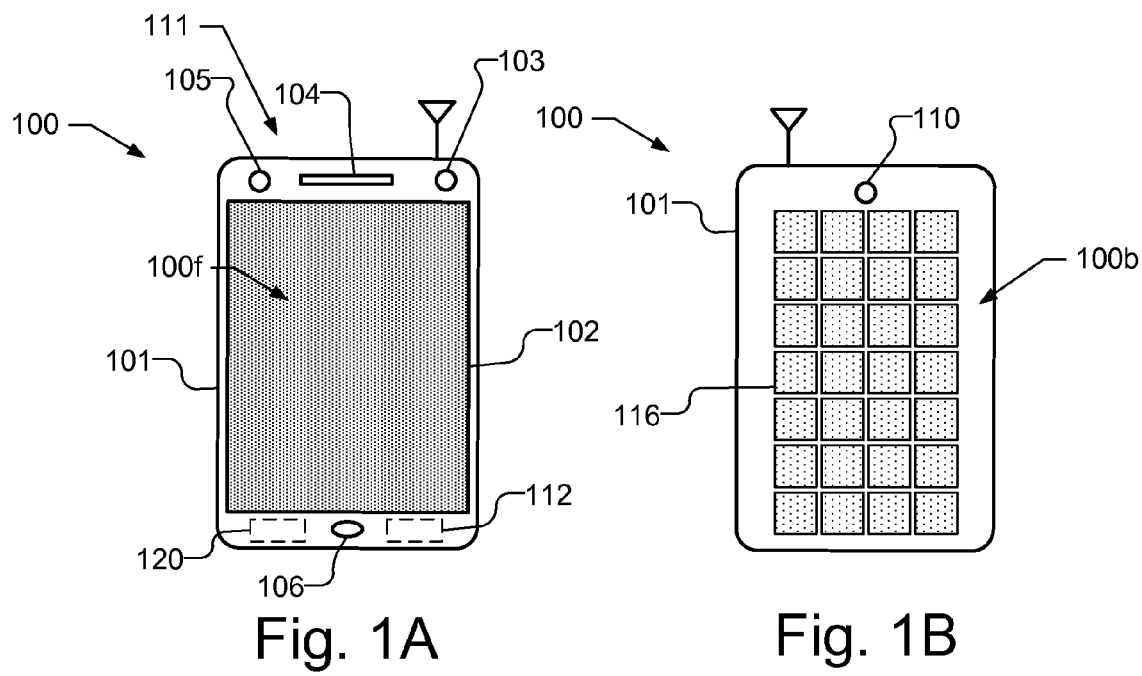
FIGS. 1A and 1B illustrate a front face and back face, respectively, of a mobile device capable of using data from one or more sensors to determine a type of surface that is in contact with the mobile device and to perform an action based on the determined type of surface.

FIGS. 1A and 1B illustrate a front face 100*f* and back face 100*b*, respectively, of a mobile device 100 capable of using data from one or more sensors that is related to a type of surface that is in contact with the mobile device and to perform an action based on the type of surface.

As used herein, a mobile device refers to any portable electronic device such as a cellular or other wireless communication device, personal communication system (PCS) device, personal navigation device (PND), Personal Information Manager (PIM), Personal Digital Assistant (PDA), laptop, tablet computer, or other suitable mobile device. The mobile device may be capable of receiving wireless communication and/or navigation signals, such as navigation positioning signals. The term "mobile device" is also intended to include devices which communicate with a personal navigation device (PND), such as by short-range wireless, infrared, wireline connection, or other connection—regardless of whether satellite signal reception, assistance data reception, and/or position-related processing occurs at the device or at the PND. Also, "mobile device" is intended to include all devices, including wireless communication devices, computers, laptops, etc. which are capable of communication with a server, such as via the Internet, WiFi®, or other network, and regardless of whether satellite signal reception, assistance data reception, and/or position-related processing occurs at the device, at a server, or at another device associated with the network. Any operable combination of the above are also considered a "mobile device."

The mobile device 100 is illustrated as including a housing 101, a display 102, which may be a touch screen display, as well as a speaker 104 and microphone 106. The mobile device 100 is further illustrated as including a number of sensors. For example, the mobile device 100 may include an ambient light sensor (ALS) 103, which reports the intensity of the light impinging on the front face of the device. In one implementation, the ALS 103 may be a camera. The mobile device 100 may further include an infrared (IR) proximity sensor 105, which reports the intensity of emitted infra-red light reflecting off objects that are near the front of the device. The mobile device 100 further includes a camera 110 on the back face 100b that may be used as a back-side light sensor. The ALS 103, IR proximity sensor 105 and camera intensity sensor 110 may be collectively referred to as proximity sensors 111. The mobile device 100 may further include motion sensors 112, such as three-axis magnetometers and/or linear accelerometers and/or gyroscopes, which may be used to provide information with respect to motion and/or orientation of the mobile device. The mobile device 100 may further include pressure sensors 116, e.g., an array of dielectric elastomers, shown on the back face 100b of the mobile device 100. If desired, pressure sensors 116 may be located on the front face 100f of the mobile device 100, e.g., on the display 102. Additional sensors that may be used by the mobile device 100 include the microphone 106 and a noise generator, which may be, e.g., the speaker 104 or a vibrator 120.

The mobile device 100 receives sensor data related to the type of surface with which it is in contact, either directly or indirectly. Based on the sensor data related to the type of surface that is detected, an action may be performed with the mobile device, e.g., automatically adjusting the mobile device settings based on a user defined profile or manufacturer pre-determined product set points. If desired, the mobile device may use the sensor data to determine the type of surface, which may be, e.g., the material of the surface and/or other characteristic of the surface, such as the hardness, texture, pattern, mass and/or size of the surface, and perform an action based on the determined type of surface.

For example, the mobile device 100 may be controlled to perform actions such as adjusting the ringer, turning on/off the WiFi® radio and/or the Bluetooth® radio, launching applications, sending a communication (e.g. "I got to work" or "I left work"), retrieving data from a local or remote data store, etc. Moreover, based on the type of surface that is detected, the mobile device 100 may determine its location, e.g., on the user's office desk, on the console of the user's car, on the kitchen countertop or coffee table at the user's house, etc. Additional information from sensors on the mobile device 100 may be used to assist in the determination of the mobile device's location. For example, environmental noises may be detected by the microphone 106, ambient light may be detected by one or more of the ALS 103, IR proximity sensor 105, and the camera intensity sensor 110, motion and/or vibration may be detected by motion sensors 112, all of which may be used to provide information relevant to the location of the mobile device 100. Additionally, a general position fix may be produced using a satellite positioning system (SPS), WiFi® network, or wireless signals and an internal clock of the mobile device 100 may be used provide time information, which may be used to assist in determining the location of the mobile device 100.

If the mobile device 100 detects a new location, e.g., based on the type of surface detected as well as any other additional information available, the mobile device 100 may prompt the user to set a location specific profile. For example, when a new location is detected, the user may be allowed to specify the actions to be taken by the mobile device, or the user may be allowed to decline setting a new location specific profile. A user may also manually prompt the mobile device 100 to set a profile for a given location. In addition, over time the mobile device may learn the user's habits for a given location and suggest changes to the location specific profile based on stored historical data for the location.

Figure 2A:
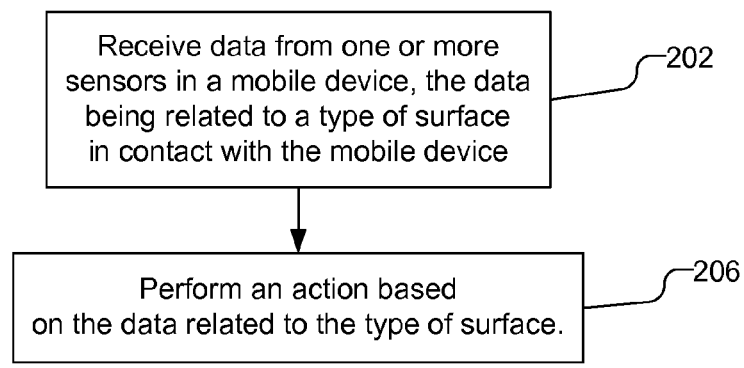
FIGS. 2A and 2B are flow charts illustrating methods of receiving data from one or more sensors related to a type of surface in contact with a mobile device and performing an action accordingly.
Figure 2B:
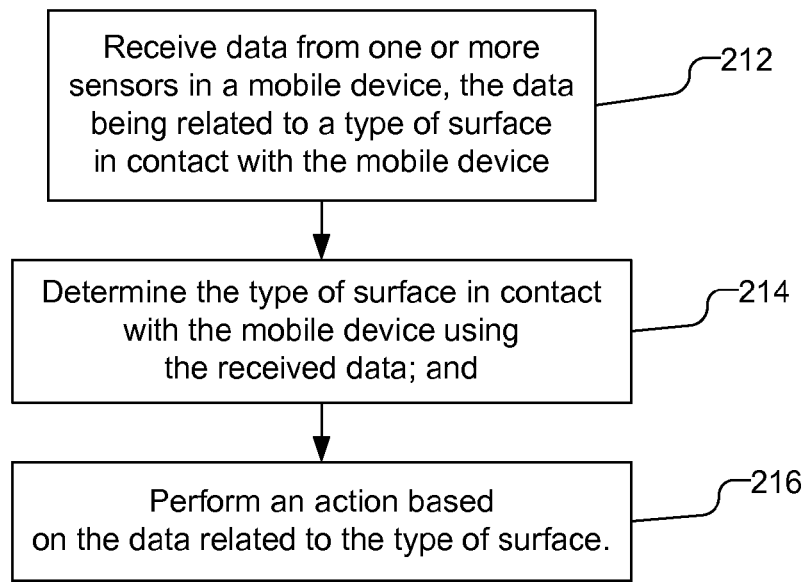

FIGS. 2A and 2B are flow charts illustrating a method of using sensor data related to the type of surface that is in contact with the mobile device and to perform an action accordingly. As illustrated in FIG. 2A, data from one or more sensors in a mobile device is received (202), where the data is related to a type of surface in contact with the mobile device. The contact may be direct or indirect, if the sensors can still receive data usable to determine the underlying surface. By way of example, the data may be received from sensors including one or more of the pressure sensors 116, light based proximity sensors 111, and the microphone 106 with a noise generator, such as speaker 104 or vibrator 120. An action is performed, e.g., by the mobile device, based on the data related to the type of surface (206). For example, action to be performed may be determined by comparing the received data to one or more libraries of sensor data stored in a database, which may either local to the mobile device 100 or accessible via one or more wireless protocols. The libraries of sensor data correlate the sensor data to different actions to be performed. If the sensor data does not correspond to an action to be performed, the user may be prompted to identify a desired action. For example, the mobile device 100 may alert the user that an unrecognized data related to a surface type has been received and request that the user provide user defined settings. If desired, the user prompt may be disabled. Moreover, if desired, the user may manually enter specific settings, e.g., actions, to be performed for new surfaces even when the user prompt is disabled. The actions that may be performed by the mobile device include updating settings, launching or exiting applications, etc.

FIG. 2B is similar to FIG. 2A with data from one or more sensors in a mobile device being received (212), where the data is related to a type of surface in contact with the mobile device. The contact may be direct or indirect, if the sensors can still receive data usable to determine the underlying surface. By way of example, the data may be received from sensors including one or more of the pressure sensors 116, light based proximity sensors 111, and the microphone 106 with a noise generator, such as speaker 104 or vibrator 120. The type of surface in contact with the mobile device is determined based on the data received from the sensors (214). For example, the type of surface may be determined by comparing the received data to one or more libraries of sensor data stored in a database, which may either local to the mobile device 100 or accessible via one or more wireless protocols. The libraries of sensor data correlate the sensor data to different types of surfaces. If the sensor data does not correspond to a type of surface in the library, the user may be prompted to identify the type of surface. The type of surface may include the material of the surface and/or other characteristic of the surface, such as the hardness, texture, pattern, mass and/or size of the surface. An action is performed, e.g., by the mobile device, based on the data related to the type of surface (216), and specifically on the determined type of surface. For example, an action to be performed may be determined by comparing the type of surface to one or more libraries in a database.

The action to be performed may be identified, e.g., by searching for user settings in a user profile based on the received data (FIG. 2A) or based on the determined type of surface (FIG. 2B). If a profile exists for the received data or the determined type of surface, the specified actions are performed automatically. If no profile exists, the mobile device 100 may respond by alerting the user that a new surface type has been detected and request that the user provide user defined settings. If desired, the user prompt may be disabled. Moreover, if desired, the user may manually enter specific settings, e.g., actions, to be performed for new surfaces even when the user prompt is disabled. As discussed above, the actions that may be performed by the mobile device include updating settings, launching or exiting applications, etc. If desired, the location of the mobile device may be determined based on the received data or determined type of surface with which the mobile device is in contact, and the action to be performed may be further based on the determined location. If a specific location is not associated with the type of surface, the user may be prompted to enter the location.

Additionally, after the mobile device 100 is in contact with a surface, the mobile device 100 may determine when the mobile device has moved using data from the sensors such as the pressure sensors 116, light based proximity sensors 111, or motion sensors 112. For example, the mobile device 100 may determine if it has been removed from the surface. If the mobile device determines that it is no longer in contact with a surface, a different action may be performed. For example, the ringer of the mobile device 100 may be turned off when the mobile device is placed on the user's work desk, but when the mobile device 100 determines that it is no longer in contact with the desk, the mobile device 100 turns the ringer on. Additionally or alternatively, after the mobile device 100 has determined that it has been moved, the mobile device 100 may receive a second set of data from its sensors. The mobile device may determine that a different type of surface is in contact with the mobile device based on second set of data and perform a different action based on the determined different type of surface.

Figure 3:
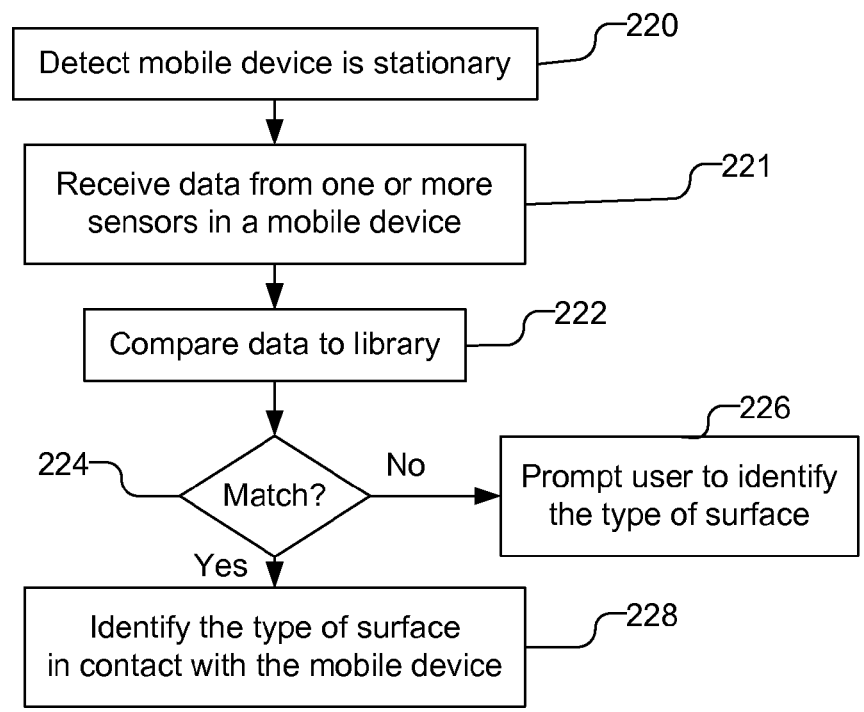
FIG. 3 is a flow chart illustrating a method of identifying the type of surface that is in contact with the mobile device.

FIG. 3 is a flow chart illustrating a method of identifying the type of surface that is in contact with the mobile device. The mobile device 100 may detect that it is has transitioned from a moving state to a stationary state, e.g., using data from motion sensors 112 (220) and accordingly may begin a routine to determine the type of surface with which it is in contact. Thus, as discussed above, in reference to FIGS. 2A and 2B, data from one or more sensors in a mobile device is received (221). The data received by the sensors may then be compared against a library that correlates the sensor data to different types of surfaces (222). The library may be a pre-generated library, e.g., provided by the manufacturer of the mobile device, and/or may be built or expanded by the user. If no match is found (224), the user may be prompted to identify the type of surface (226), which is then stored in the library with the corresponding sensor data. If desired, the user may initiate a surface calibration to identify the type of surface associated with the received data without prompting from the mobile device. If a match in the library is found (224), the type of surface in contact with the mobile device is identified (228).

An example of sensors that may be used are the pressure sensors 116 on the backside of mobile device 100, as illustrated in FIG. 1B. Pressure sensors 116 may be, e.g., an array of dielectric elastomers, capable of detecting very small changes in pressure along the back of the device. The array of dielectric elastomers may also be used to determine surface roughness as well as repeating patterns of surface contact pressure. When the mobile device 100 is initially set down on the surface of an object, vibrations or motion in the object are produced, which can be detected as reflected pressure waves by the pressure sensors 116. By way of example, the pressure sensors 116 may continually measure pressure waves, where the pressure waves detected immediately after the mobile device 100 is detected to be stationary (step 220 in FIG. 3) are used as the measurement of reflected pressure waves caused by setting down the mobile device 100. Additionally or alternatively, the vibrator 120 may be pulsed and/or speaker 104 may emit sound waves to produce pressure waves (i.e., vibration) in the surface of the object, while the pressure sensors 116 detect, e.g., the attenuation of the vibration in the surface to determine the hardness, texture, mass and/or size of the surface which the mobile device 100 is in contact. With the use of multiple pressure sensors, e.g., in an array on the backside of the mobile device, the pressure sensors 116 may be used to detect the attenuation of the vibration in the surface from different directions. Thus, the measured amplitude of the reflected vibrations can be used to determine the type of surface based on vibration absorption/reflection constants for a particular material or item, as stored in the library (228). Additionally, when resting on a surface, pressure induced simply by the weight and orientation of the mobile device 100 (which can be measured by motion sensors 112), as well as the surface characteristics, e.g., texture and hardness, of the surface can be measured by the pressure sensors 116. As the weight and orientation of the mobile device 100 are known, the surface characteristics can be determined using the library.

Other sensors that may be used to identify the type of surface in contact with the mobile device are the light based proximity sensors 111. The light based proximity sensors 111, such as the camera intensity sensor 110 on the back face 100b, may be used to measure the reflectivity of the surface. The light that is reflected from the surface may be ambient light, which may be calibrated using, e.g., the ALS 103, or light from a light emitting diode (LED) on the mobile device 100, such as the flash, which has a known intensity. If the front face 100f of the mobile device 100 is in contact with the surface, the IR proximity sensor 105 and/or the ALS 103 may be used to measure the surface reflectivity. If desired, an IR proximity sensor 105 and/or ALS 103 may be present on the back face 100b of the mobile device 100 and may be used along with or in place of the camera intensity sensor 110. The reflectivity data may be used to determine the surface material, which may be used to distinguish different types of surface, e.g., a soft fabric couch and a wooden coffee table. In addition, a camera can be used to analyze the color and repeating patterns in a surface which may also be compared against a library of known materials. Thus, by comparing the data from the light based proximity sensors 111 to a library of known reflectivity data (222), the surface with which the mobile device 100 is in contact may be determined (228). If no match is found, the user may be prompted to initiate a surface calibration to add the reflectivity data for a specific type of surface to the library.

Another example of sensors that may be used by the mobile device 100 to determine the type of surface are sound sensors (e.g., microphone 106), which may be used in conjunction with a noise generator (e.g., speaker 104 or vibrator 120), to determine the audio characteristics of the surface, such as sound absorption, the resonant frequency, etc. For example, the speaker 104 may be used to emit sound waves while the microphone 106 is used to measure the reflected sound waves. Alternatively, the vibrator 120 may pulse and the noise caused by the resulting vibration of the mobile device 100 on the surface is measured by the microphone 106. If present on mobile device 100, multiple microphones may be used to the audio characteristics of the surface from different directions. The amplitude of the reflected waves can be used to determine the surface based on sound absorption/reflection constants for a particular material or item. Based on a library of known audio characteristics, the surface with which the mobile device 100 is in contact may be determined (228). As discussed above, the user may initiate a surface calibration to identify the type of surface associated with the received data.

If more than one type of sensor is used to determine the type of surface in contact with the mobile device 100, the library look up may require confirmation from all or a subset of the sensors to identify the type of surface. Moreover, if desired, the data from some sensors, such as pressure sensors 116 and the microphone 106 with noise generator may be give more weight than other sensors, such as the light based proximity sensors 111, when searching for the type of surface due to, e.g., greater reliability of some sensors.

Figure 4:
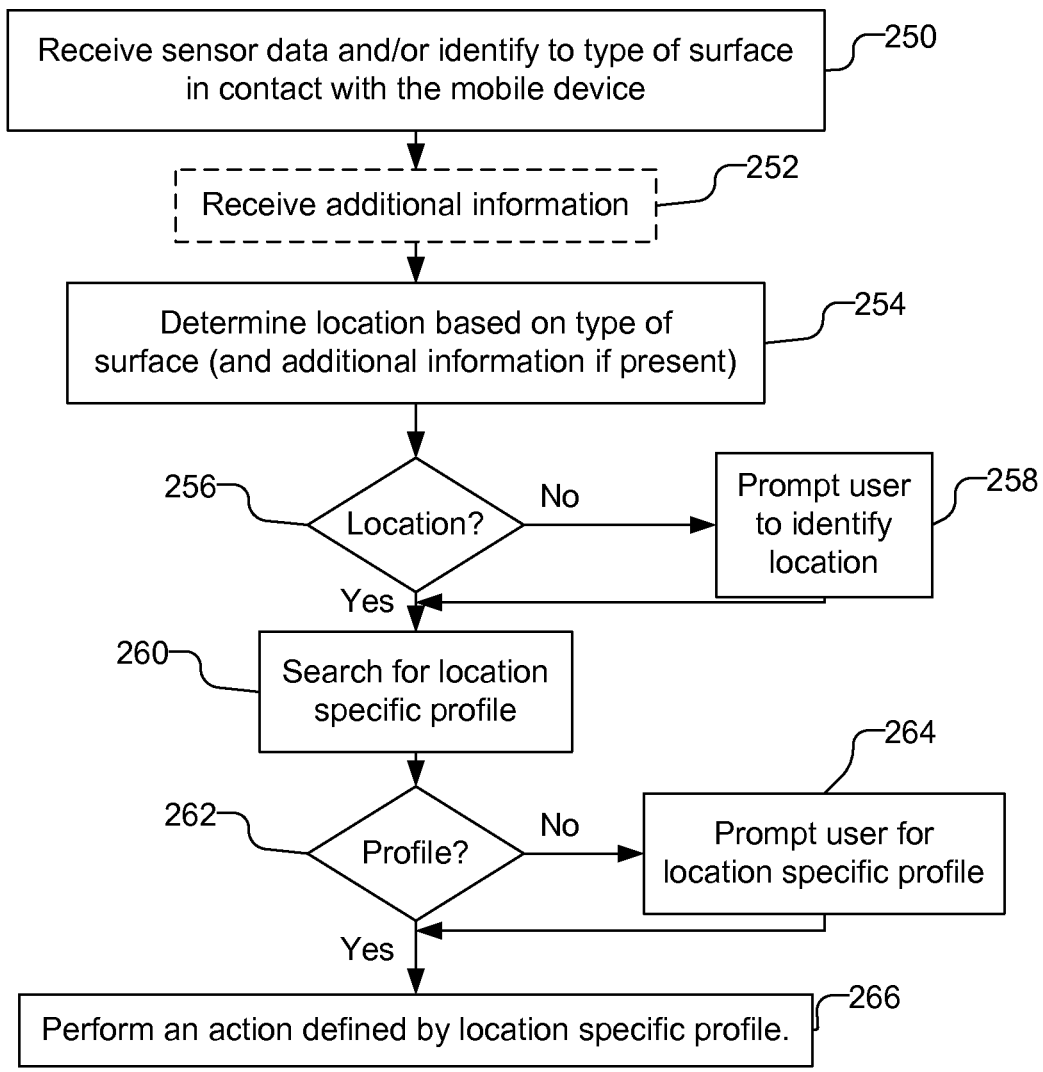
FIG. 4 is a flow chart illustrating a method of controlling the mobile device based on the location of the mobile device, which is based on the type of surface in contact with the mobile device.

As discussed above, an action is performed based on the received data that is related to the type of surface. If desired, the action to be performed may be further based on the location of the mobile device, which is determined based on, e.g., the received data or the determined type of surface in contact with the mobile device. FIG. 4 is a flow chart illustrating a method of controlling the mobile device based on the location of the mobile device. As illustrated, the sensor data related to the type of surface and/or the identity of the type of surface is received (250). To determine a location of the mobile device based on the type of surface, the mobile device should be placed on a location specific surface. For example, if the mobile device is placed in a pocket, the mobile device may detect the type of surface (e.g., cloth material) and be able to determine that it is in the user's pocket, but the mobile device would not be able to determine the user's location, e.g., in a car or sitting at a desk. Accordingly, additional information may also be received (252) which may be useful to identify locations when the surface is not location specific. Additional information may be any information that may be relevant to the location of the mobile device, but may be unrelated to the type of surface with which the mobile device is in contact. For example, additional information may include a general position fix, which may be determined wirelessly, e.g., using an SPS, WiFi® signals, or cellular signals. Additional information may also include detected WiFi® or Bluetooth® devices with known locations, environmental sounds detected by the microphone 106 (e.g. office air conditioning, the line-frequency hum of fluorescent lighting, engine and/or road noise). Another example of additional information that may be used is the current day and time that is associated with the user's routine, e.g., the user's typical location at specific times and days of the week, and which may be updated automatically and/or manually and stored in a database. Additional information may be useful for determining the location of the mobile device, e.g., if a particular type of surface is found in more than one location. For example, the identification of a polished wooden table as the type of surface in contact with the mobile device may not provide enough information to determine the location of the mobile device if a polished wooden table is present in the user's house and office. However, with additional information, such as a general position fix, detected wireless devices with known locations, the presence or absence of noise from office air conditioning, and/or the date and time and the user's typical work hours, the ambiguity with respect to location may be resolved.

Based on the received data and/or the identity of the type of surface, as well as any additional information that is provided, the location of the mobile device may be determined (254), e.g., using a library of locations stored in a database, which may either local to the mobile device 100 or accessible via one or more wireless protocols. The library of locations may be built over time by the user to correlate locations with sensor data related to the type of surfaces and/or identity of the type of surfaces, as well as any additional information. If no location can be determined based on the available data (256), the user may be prompted to identify the location (258). If a location can be determined based on the available information (256), a search is performed for a location specific profile (260), which may be stored in a database. The location specific profile identifies the desired action or actions to be performed by the mobile device based on a determined location. It should be understood that the location specific profile may be part of the library of locations and thus, the location determination (254) and search for a location specific profile (256) may be performed together. The location specific profile may specify actions such as enabling/disabling radios, e.g., WiFi® and/or Bluetooth®, adjusting ringer volume, enabling/disabling specific apps, enabling/disabling a music player, enabling/disabling a satellite positioning system, enabling/disabling streaming of video apps, sending a communication (e.g. "I got to work" or "I left work"), retrieving data from a local or remote data store, etc. If no location specific profile is found (262), the user may be prompted to input the desired actions for a location specific profile (264). If a location specific profile is found (262), the action or actions defined by the location specific profile is performed (266).

In general, the number of locations that a user would routinely set down the mobile device is limited. Accordingly, the number of times a calibration routine, e.g., step 226 in FIG. 3, or steps 258 or 264 in FIG. 4, would need to be employed to learn the properties of the surface, the location, or the desired location specific profile may be limited to only a few locations, e.g. the user's office desk, nightstand table, coffee table, automobile console, etc.

Thus, by way of example, if a user picks up the mobile device 100 from one surface and brings the mobile device to another surface, the mobile device 100 may detect that a change in location has occurred, e.g., using SPS, WiFi®, Bluetooth®, motion sensors 112, etc. When the mobile device 100 detects that it is stationary, the mobile device 100 will attempt to determine the type of surface with which it is in contact. For example, the mobile device 100 may compare the output of the pressure sensors 116, light based proximity sensors 111, sound sensor (e.g., microphone 106) against one or more libraries of known surfaces.

Figure 5:
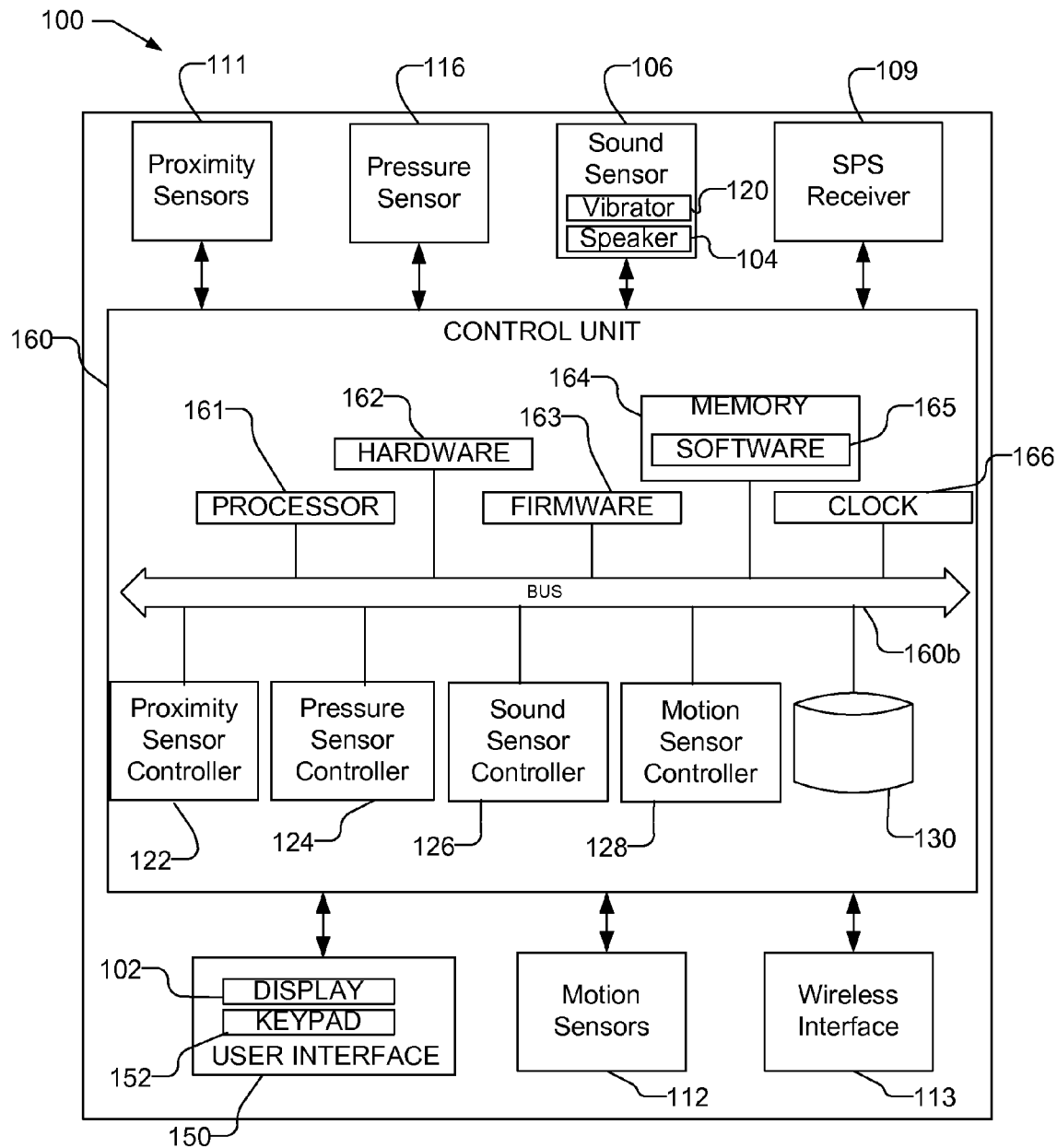
FIG. 5 is a block diagram of a mobile device capable of using data from one or more sensors to determine the type of surface in contact with the mobile device and to perform an action based on the type of surface.

FIG. 5 is a block diagram of a mobile device 100 capable of using sensor data related to a type of surface in contact with the mobile device and to perform an action, as described above. The mobile device 100 includes a number of sensors, such as light based proximity sensors 111, motion sensors 112, pressure sensors 116, and a sound sensor 106, which may be a microphone or other sound sensor, which may be used with the speaker 104 and/or vibrator 120 as a noise generator. The mobile device 100 may further include a user interface 150 that includes the display 102, as well as a keypad 152 or other input device through which the user can input information into the mobile device 100. If desired, the keypad 152 may be obviated by integrating a virtual keypad into the display 102 with a touch sensor (or gesture control). The display 102 may also include pressure sensors, similar to pressure sensors 116, if desired. Of course, mobile device 100 may include other elements such as the SPS receiver 109, wireless interface 113, etc.

The SPS receiver 109 may be used with any SPS, which are well known, and may include Global Navigation Satellite System (GNSS) such as Global Positioning System (GPS), Galileo, Glonass or Compass. The SPS may also or alternatively include regional systems, such as, e.g., Quasi-Zenith Satellite System (QZSS) over Japan, Indian Regional Navigational Satellite System (IRNSS) over India, Beidou over China, etc., and/or various augmentation systems (e.g., an Satellite Based Augmentation System (SBAS)) that may be associated with or otherwise enabled for use with one or more global and/or regional navigation satellite systems.

The wireless interface 113 may use various wireless communication networks such as a wireless wide area network (WWAN), a wireless local area network (WLAN), a wireless personal area network (WPAN), and so on. The term "network" and "system" are often used interchangeably. A WWAN may be a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, Long Term Evolution (LTE), and so on. A CDMA network may implement one or more radio access technologies (RATs) such as cdma2000, Wideband-CDMA (W-CDMA), and so on. Cdma2000 includes IS-95, IS-2000, and IS-856 standards. A TDMA network may implement Global System for Mobile Communications (GSM), Digital Advanced Mobile Phone System (D-AMPS), or some other RAT. GSM and W-CDMA are described in documents from a consortium named "3rd Generation Partnership Project" (3GPP). Cdma2000 is described in documents from a consortium named "3rd Generation Partnership Project 2" (3GPP2). 3GPP and 3GPP2 documents are publicly available. A WLAN may be an IEEE 802.11x network, and a WPAN may be a Bluetooth® network, an IEEE 802.15x, or some other type of network. Moreover, any combination of WWAN, WLAN and/or WPAN may be used.

The mobile device 100 also includes a control unit 160 that is connected to and communicates with the light based proximity sensors 111, motion sensors 112, pressure sensors 116, and sound sensor 106, as well as any other devices, such as the SPS receiver 109 and wireless interface 113. The control unit 160 accepts and processes the data provided by the light based proximity sensors 111, motion sensors 112, pressure sensors 116, and sound sensor 106. The control unit 160 may be provided by a bus 160b, processor 161 and associated memory 164, hardware 162, software 165, and firmware 163, and a clock 166. The control unit 160 may include a proximity sensor controller 122, pressure sensor controller 124, sound sensor controller 126, and motion sensor controller 128, as well as a database 130 containing one or more libraries, e.g., for the type of surface, location, and desired profile such as a location specific profile, as discussed above. If desired, the database 130 may be stored remotely and be available to mobile device 100 through, e.g., wireless interface, using one or more wireless protocols.

The proximity sensor controller 122, pressure sensor controller 124, sound sensor controller 126, and motion sensor controller 128 are illustrated separately from processor 161 for clarity, but may be part of the processor 161 or implemented in the processor based on instructions in the software 165 which is run in the processor 161. It will be understood as used herein that the processor 161 can, but need not necessarily include, one or more microprocessors, embedded processors, controllers, application specific integrated circuits (ASICs), digital signal processors (DSPs), and the like. The term processor is intended to describe the functions implemented by the system rather than specific hardware. Moreover, as used herein the term "memory" refers to any type of computer storage medium, including long term, short term, or other memory associated with the mobile device, and is not to be limited to any particular type of memory or number of memories, or type of media upon which memory is stored.

The mobile device includes means for receiving data from one or more sensors in a mobile device, wherein the data is related to a type of surface in contact with the mobile device, which may be, e.g., at least one of a microphone 106 and a noise generator, such as speaker 104 or vibrator 120, a light based proximity sensor 111, and pressure sensors 116 configured to detect a texture of the surface, along with their respective controllers 126, 122, and 124. The mobile device further include means for performing an action based on the data related to the type of surface in contact with the mobile device, which may be, e.g., the database 130 and the processor 161. The mobile device may further includes a means for determining the type of surface in contact with the mobile device using the received data, which may be, e.g., sound sensor controller 126, proximity sensor controller 122, or pressure sensor controller 124, along with the database 130. The mobile device may further include a means for determining a location for the mobile device based on the determined type of surface and a means for using the location to identify the action to perform, which may be, e.g., the database 130. The mobile device may further include a means for receiving additional data unrelated to the type of surface in contact with the mobile device, which may include the SPS receiver 109, wireless interface 113, motion sensors 112, clock 166, sound sensor 106, etc. The mobile device may further include a means for using the additional data with the determined type of surface for determining the location, which may be, e.g., the database 130.

The methodologies described herein may be implemented by various means depending upon the application. For example, these methodologies may be implemented in hardware 162, firmware 163, software 165, or any combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in memory 164 and executed by the processor 161. Memory may be implemented within or external to the processor 161. If implemented in firmware and/or software, the functions may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method comprising:
    determining that a mobile device has transitioned from a moving state to a stationary state;
    receiving data from one or more sensors in the mobile device, wherein the data is related to a type of surface in contact with the mobile device;
    determining the type of surface in contact with the mobile device using the received data in response to determining that the mobile device is in the stationary state;
    determining a location for the mobile device based on the type of surface in contact with the mobile device;
    performing an action based on the location determined based on the type of surface in contact with the mobile device;
    determining the mobile device has moved;
    receiving a second set of data from the one or more sensors;
    determining a different type of surface in contact with the mobile device using the second set of data; and
    performing a different action based on the determined different type of surface.

2. The method of claim 1, further comprising:
    determining the mobile device has been removed from the surface;
    performing a second different action after the mobile device has been removed from the surface.

3. The method of claim 1, wherein the one or more sensors comprise a microphone and a noise generator, wherein the microphone detects sound produced by the noise generator and reflected by the surface.

4. The method of claim 3, wherein the noise generator is at least one of a speaker and a vibrator.

5. The method of claim 1, wherein the one or more sensors comprise a light based proximity sensor.

6. The method of claim 1, wherein the one or more sensors comprise pressure sensors configured to detect at least one of a texture of the surface and pressure waves reflected from the surface.

7. The method of claim 6, wherein the pressures waves are produced by at least one of setting down the mobile device and a noise generator.

8. The method of claim 7, wherein the noise generator is at least one of a speaker and a vibrator.

9. The method of claim 6, wherein the pressure sensors comprises dielectric elastomers.

10. The method of claim 1, wherein performing the action comprises controlling the mobile device to perform the action.

11. The method of claim 1, determining the type of surface in contact with the mobile device using the received data comprises determining at least one of a hardness, texture, pattern, mass and size of the surface.

12. The method of claim 1, determining the type of surface in contact with the mobile device using the received data comprises determining a material of the surface.

13. A method comprising:
    determining that a mobile device has transitioned from a moving state to a stationary state;
    receiving data from one or more sensors in the mobile device, wherein the data is related to a type of surface in contact with the mobile device;
    determining the type of surface in contact with the mobile device using the received data in response to determining that the mobile device is in the stationary state;
    determining a location for the mobile device based on the type of surface in contact with the mobile device, wherein determining the location for the mobile device comprises:
        receiving additional data, wherein the additional data comprises at least one of a general position fix, detected wireless devices, environmental sounds, and time associated with a user's routine; and
        using the additional data with the type of surface for determining the location; and
    performing an action based on the location determined based on the type of surface in contact with the mobile device.

14. A mobile device comprising:
    one or more sensors;
    one or more motion sensors; and
    a processor coupled to receive data from the one or more sensors and motion data from the one or more motion sensors, wherein the data is related to a type of surface in contact with the mobile device, the processor being configured to determine that the mobile device has transitioned from a moving state to a stationary state using the motion data; determine the type of surface in contact with the mobile device using the received data in response to a determination that the mobile device is in the stationary state; determine a location for the mobile device based on the type of surface in contact with the mobile device; and perform an action based on the location determined based on the type of surface in contact with the mobile device, wherein the processor is further configured to determine when the mobile device has moved, receive a second set of data from the one or more sensors, determine a different type of surface in contact with the mobile device using the second set of data, and perform a different action based on the determined different type of surface.

15. The mobile device of claim 14, wherein the processor is further configured to determine when the mobile device has been removed from the surface and perform a second different action after the mobile device has been removed from the surface.

16. The mobile device of claim 14, wherein the one or more sensors comprise a microphone and a noise generator, wherein the microphone detects sound produced by the noise generator and reflected by the surface.

17. The mobile device of claim 16, wherein the noise generator is at least one of a speaker and a vibrator.

18. The mobile device of claim 14, wherein the one or more sensors comprise a light based proximity sensor.

19. The mobile device of claim 14, wherein the one or more sensors comprise pressure sensors configured to detect at least one of a texture of the surface and pressure waves reflected from the surface.

20. The mobile device of claim 19, wherein the pressures waves are produced by at least one of setting down the mobile device and a noise generator.

21. The mobile device of claim 20, wherein the noise generator is at least one of a speaker and a vibrator.

22. The mobile device of claim 19, wherein the pressure sensors comprises dielectric elastomers.

23. The mobile device of claim 14, wherein the processor is configured to determine the type of surface in contact with the mobile device by being configured to determine at least one of a hardness, texture, pattern, mass and size of the surface.

24. The mobile device of claim 14, wherein the processor is configured to determine the type of surface in contact with the mobile device by being configured to determine a material of the surface.

25. A mobile device comprising:
one or more sensors;
one or more motion sensors; and
a processor coupled to receive data from the one or more sensors and motion data from the one or more motion sensors, wherein the data is related to a type of surface in contact with the mobile device, the processor being configured to determine that the mobile device has transitioned from a moving state to a stationary state using the motion data; determine the type of surface in contact with the mobile device using the received data in response to a determination that the mobile device is in the stationary state; determine a location for the mobile device based on the type of surface in contact with the mobile device, wherein the processor is configured to determine the location for the mobile device by being configured to receive additional data from the one or more sensors, wherein the additional data comprises at least one of a general position fix, detected wireless devices, environmental sounds, and time associated with a user's routine, and to use the additional data with the type of surface to determine the location; and perform an action based on the location determined based on the type of surface in contact with the mobile device.

26. A mobile device comprising:
means for determining that the mobile device has transitioned from a moving state to a stationary state;
means for receiving data from one or more sensors in the mobile device, wherein the data is related to a type of surface in contact with the mobile device;
means for determining the type of surface in contact with the mobile device using the received data in response to determining that the mobile device is in the stationary state;
means for determining a location for the mobile device based on the type of surface in contact with the mobile device;
means for performing an action based on the location determined based on the type of surface in contact with the mobile device;
means for determining the mobile device has moved;
means for receiving a second set of data from the one or more sensors;
means for determining a different type of surface in contact with the mobile device using the second set of data; and
means for performing a different action based on the determined different type of surface.

27. The mobile device of claim 26, wherein the means for receiving data comprises at least one of a microphone and a noise generator, a light based proximity sensor, and pressure sensors.

28. A mobile device comprising:
means for determining that the mobile device has transitioned from a moving state to a stationary state;
means for receiving data from one or more sensors in the mobile device, wherein the data is related to a type of surface in contact with the mobile device;
means for determining the type of surface in contact with the mobile device using the received data in response to determining that the mobile device is in the stationary state;
means for determining a location for the mobile device based on the type of surface in contact with the mobile device, wherein the means for determining the location for the mobile device comprises:
means for receiving additional data unrelated to the type of surface in contact with the mobile device, wherein the additional data comprises at least one of a general position fix, detected wireless devices, environmental sounds, and time associated with a user's routine; and
means for using the additional data with the type of surface for determining the location; and
means for performing an action based on the location determined based on the type of surface in contact with the mobile device.

29. A non-transitory computer-readable medium including program code stored thereon, comprising:
program code to determine that a mobile device has transitioned from a moving state to a stationary state;
program code to receive data from one or more sensors in the mobile device, wherein the data is related to a type of surface in contact with the mobile device;
program code to determine the type of surface in contact with the mobile device using the received data in response to determining that the mobile device is in the stationary state;
program code to determine a location for the mobile device based on the type of surface in contact with the mobile device;
program code to perform an action based on the location determined based on the type of surface in contact with the mobile device;
program code to determine the mobile device has moved;
program code to receive a second set of data from the one or more sensors;
program code to determine a different type of surface in contact with the mobile device using the second set of data; and
program code to perform a different action based on the determined different type of surface.

30. A non-transitory computer-readable medium including program code stored thereon, comprising:
program code to determine that a mobile device has transitioned from a moving state to a stationary state;
program code to receive data from one or more sensors in the mobile device, wherein the data is related to a type of surface in contact with the mobile device;
program code to determine the type of surface in contact with the mobile device using the received data in response to determining that the mobile device is in the stationary state;
program code to determine a location for the mobile device based on the type of surface in contact with the mobile device, wherein the program code to determine the location for the mobile device comprises program code to determine the location using additional received data that is unrelated to the type of surface in contact with the mobile device along with the determined type of surface, wherein the additional data comprises at least one of a general position fix, detected wireless devices, environmental sounds, and time associated with a user's routine; and
program code to perform an action based on the location determined based on the type of surface in contact with the mobile device.

* * * * *